(12) United States Patent
Hammerland et al.

(10) Patent No.: US 11,737,811 B2
(45) Date of Patent: Aug. 29, 2023

(54) ELECTROSURGICAL FORCEPS

(71) Applicant: Covidien LP, Mansfield, MA (US)

(72) Inventors: John A. Hammerland, Arvada, CO (US); William E. Robinson, Boulder, CO (US); Stephen J. Stamm, Wheat Ridge, CO (US)

(73) Assignee: COVIDIEN LP, Mansfield, MA (US)

( * ) Notice: Subject to any disclaimer, the term of this patent is extended or adjusted under 35 U.S.C. 154(b) by 579 days.

(21) Appl. No.: 16/722,289

(22) Filed: Dec. 20, 2019

(65) Prior Publication Data

US 2020/0197075 A1 Jun. 25, 2020

Related U.S. Application Data

(60) Provisional application No. 62/782,850, filed on Dec. 20, 2018.

(51) Int. Cl.
*A61B 18/14* (2006.01)
*A61B 17/29* (2006.01)
(Continued)

(52) U.S. Cl.
CPC .. *A61B 18/1445* (2013.01); *A61B 2017/2929* (2013.01); *A61B 2018/0063* (2013.01); *A61B 2018/00178* (2013.01); *A61B 2018/00589* (2013.01); *A61B 2018/00595* (2013.01); *A61B 2018/126* (2013.01); *A61B 2018/1455* (2013.01)

(58) Field of Classification Search
CPC ........ A61B 18/1445; A61B 2017/2929; A61B 2018/00178; A61B 2018/00589; A61B 2018/00595; A61B 2018/0063; A61B 2018/126; A61B 2018/1455; A61B 2018/00202
See application file for complete search history.

(56) References Cited

U.S. PATENT DOCUMENTS 7,255,697 B2 8/2007 Dycus et al.
8,461,744 B2 6/2013 Wiener et al.
(Continued)

FOREIGN PATENT DOCUMENTS

EP 2982328 A1 * 2/2016 ............ A61B 17/29
EP 2982328 A1 2/2016
(Continued)

OTHER PUBLICATIONS

Extended European Search Report for application No. 19218151.9 dated May 19, 2020.

*Primary Examiner* — Khadijeh A Vahdat
*Assistant Examiner* — Mystee Nguyen Delgado
(74) *Attorney, Agent, or Firm* — Carter, DeLuca & Farrell LLP

(57) ABSTRACT

A forceps includes an instrument housing, an elongated shaft assembly extending distally from the instrument housing, and a rotation knob assembly. The rotation knob assembly is supported in the instrument housing and includes a rotation knob and an inner housing. The rotation knob is coupled to the shaft assembly and positioned to rotate about the inner housing to rotate the elongated shaft assembly relative to the instrument housing. The inner housing is coupled to the instrument housing and supports electrical contacts configured to transmit electrical energy through the rotation knob assembly.

16 Claims, 15 Drawing Sheets

(51) Int. Cl.
    *A61B 18/00*    (2006.01)
    *A61B 18/12*    (2006.01)

(56)            References Cited

U.S. PATENT DOCUMENTS

| | | | |
|---|---|---|---|
| 8,734,476 | B2 | 5/2014 | Rhee et al. |
| 8,828,023 | B2 | 9/2014 | Neff et al. |
| 9,655,673 | B2 | 5/2017 | McCullough, Jr. et al. |
| 9,820,765 | B2 | 11/2017 | Allen, IV et al. |
| 2007/0282333 | A1* | 12/2007 | Fortson ............... B25B 23/142 606/50 |
| 2008/0208246 | A1* | 8/2008 | Livneh ............... A61B 18/1445 606/205 |
| 2009/0248020 | A1 | 10/2009 | Falkenstein et al. |
| 2012/0116363 | A1* | 5/2012 | Houser ............... G16H 20/40 606/1 |
| 2012/0136347 | A1 | 5/2012 | Brustad et al. |
| 2014/0005680 | A1 | 1/2014 | Shelton, IV et al. |
| 2017/0079641 | A1* | 3/2017 | Overmyer ......... A61B 17/07207 |

FOREIGN PATENT DOCUMENTS

| | | |
|---|---|---|
| EP | 3326548 A1 | 5/2018 |
| WO | 2011044343 A2 | 4/2011 |
| WO | 2012061640 A1 | 5/2012 |
| WO | 2016025132 A1 | 2/2016 |

\* cited by examiner

ELECTROSURGICAL FORCEPS

CROSS REFERENCE TO RELATED APPLICATIONS

This application claims the benefit of U.S. Patent Application Ser. No. 62/782,850, filed Dec. 20, 2018, the entire contents of which are incorporated by reference herein.

TECHNICAL FIELD

The present disclosure relates generally to the field of surgical instruments. In particular, the disclosure relates to an endoscopic electrosurgical forceps that is economical to manufacture and is capable of sealing and cutting relatively large tissue structures.

BACKGROUND

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode to enable the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces or tissue engaging surfaces of the jaw members. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled: the pressure applied to the vessel and the gap distance established between the electrodes.

Both the pressure and the gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied, the tissue may have a tendency to move before an adequate seal can be generated. The gap distance between tissue engaging surfaces of a typical effective tissue seal is optimally between about 0.001 and about 0.010 inches. Below this range, the seal may shred or tear, and above this range, the vessel walls may not be effectively joined. Closure pressures for sealing large tissue structures preferably fall within the range of about 3 $kg/cm^2$ to about 16 $kg/cm^2$.

SUMMARY

The present disclosure relates to an electrosurgical apparatus and methods for performing electrosurgical procedures. More particularly, the present disclosure relates to electrosurgically sealing tissue.

The present disclosure describes an electrosurgical instrument for treating tissue that is economical to manufacture and is capable of sealing and cutting relatively large tissue structures.

According to one aspect of the present disclosure, a forceps includes an instrument housing, an elongated shaft assembly extending distally from the instrument housing, and a rotation knob assembly. The rotation knob assembly is supported in the instrument housing and includes a rotation knob and an inner housing. The rotation knob is coupled to the shaft assembly and positioned to rotate about the inner housing to rotate the elongated shaft assembly relative to the instrument housing. The inner housing is coupled to the instrument housing and supports electrical contacts configured to transmit electrical energy through the rotation knob assembly.

In some embodiments, the rotation knob assembly may include an inner contact ring and an outer contact ring that are electrically isolated from one another. The inner contact ring may have a diameter and the outer contact may have a diameter. The diameter of the inner contact ring may be different from the diameter of the outer contact ring.

In various embodiments, a first contact spring may be in contact with the inner contact ring and a second contact spring may be in contact with the outer contact ring. The first and second contact springs may be supported by the inner housing and electrically isolated from one another.

In embodiments, the rotation knob may include a shaft mount that defines a passageway for receiving the elongated shaft assembly therein.

In some embodiments, the rotation knob may define an outer ring recess positioned to receive the outer contact ring and an inner ring recess positioned to receive the inner contact ring. The inner and outer ring recesses may be separated by an isolation ring.

In certain embodiments, the elongated shaft assembly may define a longitudinal axis. The inner contact ring and the outer contact ring may be longitudinally offset from one another relative to the longitudinal axis of the elongated shaft assembly. The first contact spring may be radially closer to the longitudinal axis than the second contact spring.

According to yet another aspect of the present disclosure, an electrosurgical system is provided. The electrosurgical system includes an energy source and a forceps electrically coupled to the energy source. The forceps includes an instrument housing, an elongated shaft assembly extending distally from the instrument housing to an end effector, and a rotation knob assembly supported in the instrument housing. The rotation knob assembly includes a rotation knob and an inner housing. The rotation knob is coupled to the shaft assembly and positioned to rotate about the inner housing to rotate the elongated shaft assembly relative to the instrument housing. The inner housing is coupled to the instrument housing and supports electrical contacts configured to transmit electrical energy from the energy source through the rotation knob assembly to the end effector.

In some embodiments, the rotation knob assembly includes an inner contact ring and an outer contact ring that are electrically isolated from one another. The inner contact ring may have a diameter and the outer contact may have a diameter. The diameter of the inner contact ring may be different from the diameter of the outer contact ring.

In embodiments, a first contact spring may be in contact with the inner contact ring and a second contact spring may be in contact with the outer contact ring. The first and second contact springs may be supported by the inner housing and electrically isolated from one another.

In various embodiments, the rotation knob may include a shaft mount defining a passageway for receiving the elongated shaft assembly therein.

In certain embodiments, the rotation knob may define an outer ring recess positioned to receive the outer contact ring and an inner ring recess positioned to receive the inner contact ring. The inner and outer ring recesses may be separated by an isolation ring.

In embodiments, the elongated shaft assembly may define a longitudinal axis. The inner contact ring and the outer contact ring may be longitudinally offset from one another relative to the longitudinal axis of the elongated shaft assembly. The first contact spring may be radially closer to the longitudinal axis than the second contact spring.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1A:
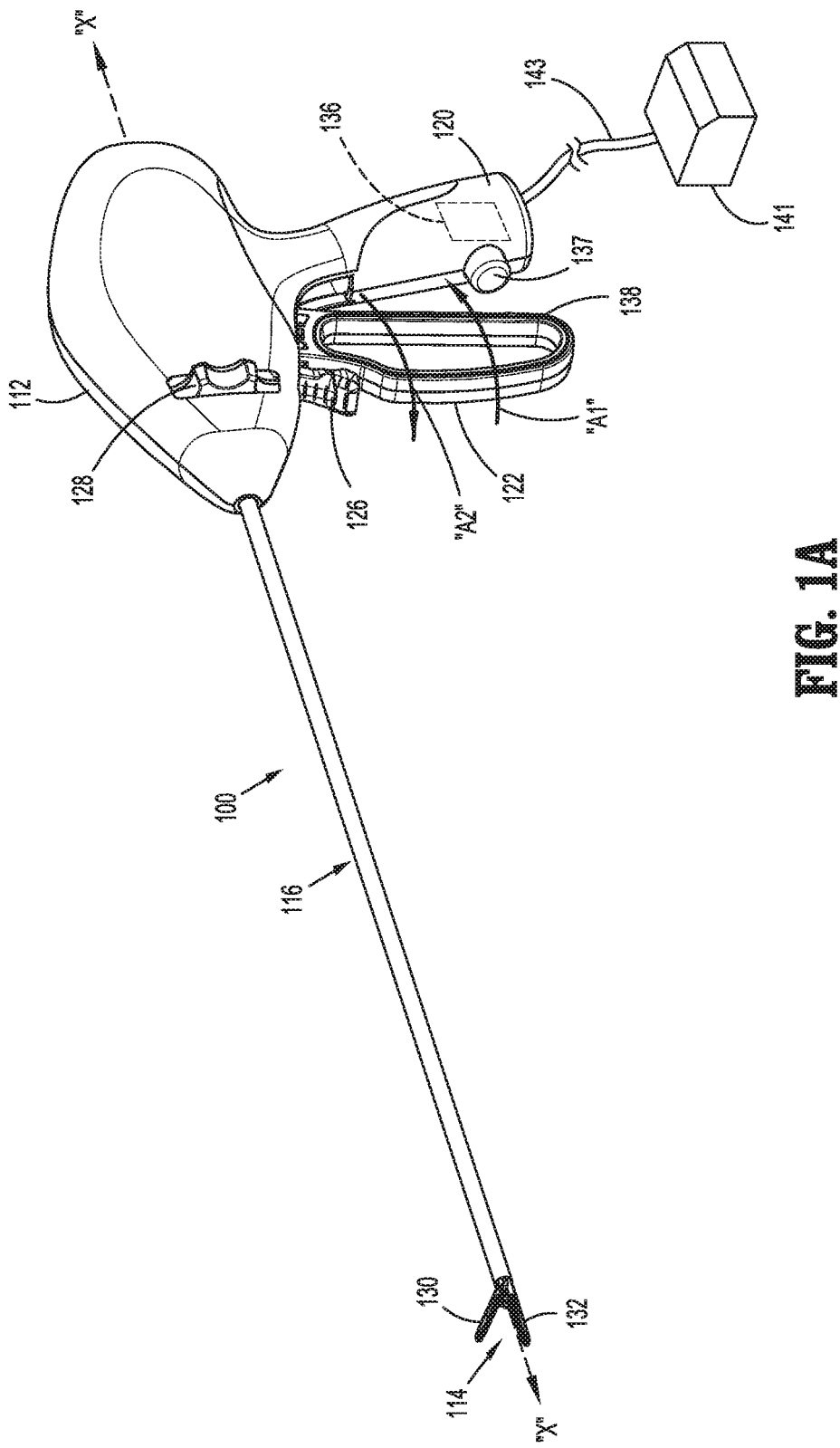
FIG. 1A is a perspective view of an electrosurgical forceps according to an embodiment of the present disclosure.

Embodiments of the presently disclosed electrosurgical forceps are described in detail with reference to the drawings, in which like reference numerals designate identical or corresponding elements in each of the several views. As commonly known, the term "clinician" refers to a doctor, a nurse, or any other care provider and may include support personnel. Further, as is used in the art, the term "distal" refers to a position, a direction, and/or a structure, which is farther from the user, and the term "proximal" refers to a position, a direction, and/or a structure, which is closer to the user. In addition, directional terms such as front, rear, upper, lower, top, bottom, and the like are used simply for convenience of description and are not intended to limit the present disclosure.

Figure 1B:
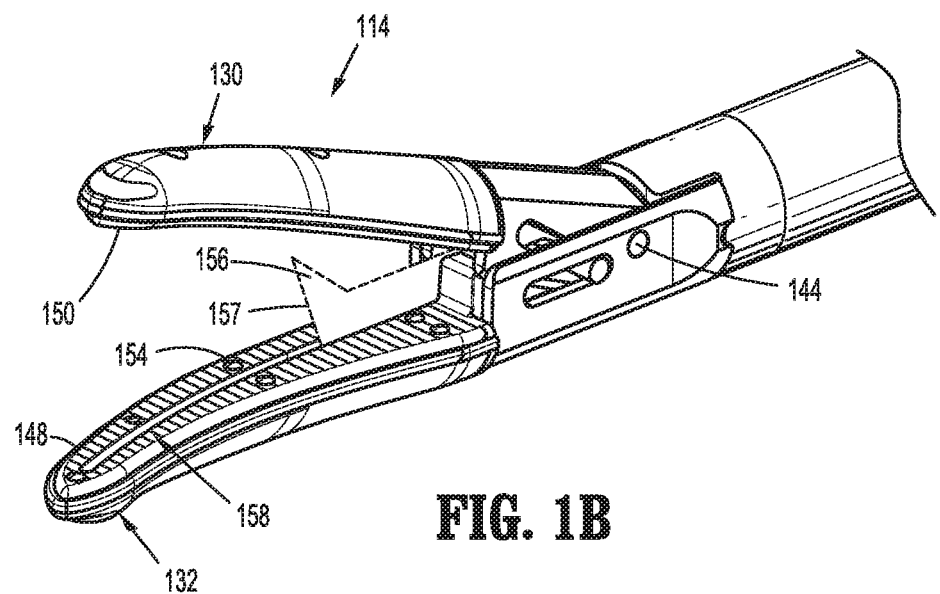
FIG. 1B is an enlarged, perspective view of an end effector of the electrosurgical forceps of FIG. 1A, the end effector illustrated in an open position.
Figure 1C:
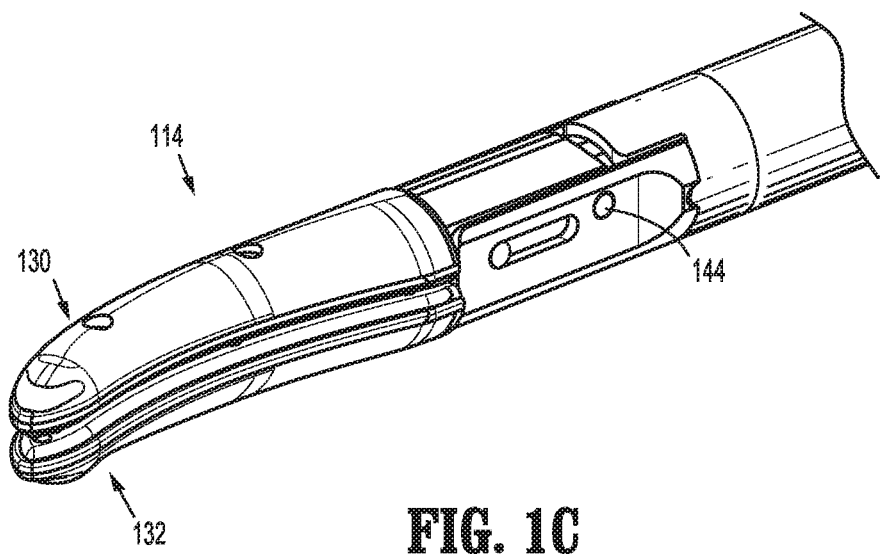
FIG. 1C is an enlarged, perspective view of the end effector of FIG. 1B illustrated in a closed position.

Referring initially to FIGS. 1A-1C, an electrosurgical forceps 100 defines a longitudinal axis "X-X" and generally includes an instrument housing 112, an elongated shaft assembly 116 that extends from instrument housing 112, and an end effector 114 supported on a distal end of elongated shaft assembly 116. Instrument housing 112 supports various actuators for remotely controlling end effector 114 through the elongated shaft assembly 116. Although this configuration is typically associated with instruments for use in laparoscopic or endoscopic surgical procedures, various aspects of the present disclosure may be practiced in connection with endoluminal procedures and with traditional open instruments.

To mechanically control end effector 114 of electrosurgical forceps 100, instrument housing 112 supports a stationary handle 120, a movable handle 122, a trigger 126 and a rotation knob assembly 128. Movable handle 122 of instrument housing 112 is operable to move end effector 114 between an open position (FIGS. 1A and 1B) in which a pair of opposed jaw members 130, 132 are disposed in spaced relation relative to one another, and a closed or clamping position (FIG. 1C) in which jaw members 130, 132 are closer together. Approximation of movable handle 122 toward stationary handle 120, as indicated by arrow "A1," serves to move end effector 114 to the closed position. Separation of movable handle 122 away from stationary handle 120, as indicated by arrow "A2," serves to move end effector 114 to the open position. Trigger 126 is operable to extend and retract a knife blade 156 (FIG. 1B) through end effector 114 when end effector 114 is in the closed position (FIG. 1C). Rotation knob assembly 128 serves to rotate elongated shaft assembly 116 and end effector 114 about longitudinal axis "X-X" of electrosurgical forceps 100.

To electrically control end effector 114 of electrosurgical forceps 100, stationary handle 120 of instrument housing 112 of forceps 100 supports a depressible button 137 that is operable by a clinician to selectively initiate and terminate delivery of electrosurgical energy to end effector 114. Depressible button 137 is mechanically coupled to a switch 136 disposed within stationary handle 120. Upon proximal movement of movable handle 122 toward an actuated or proximal position, as illustrated by arrow "A1," button 137 is configured to engage a button activation post 138 that extends from a proximal side of movable handle 122. Switch 136 is in electrical communication with an electrosurgical generator 141 via a cable 143 that extends from instrument housing 112.

Figure 2:
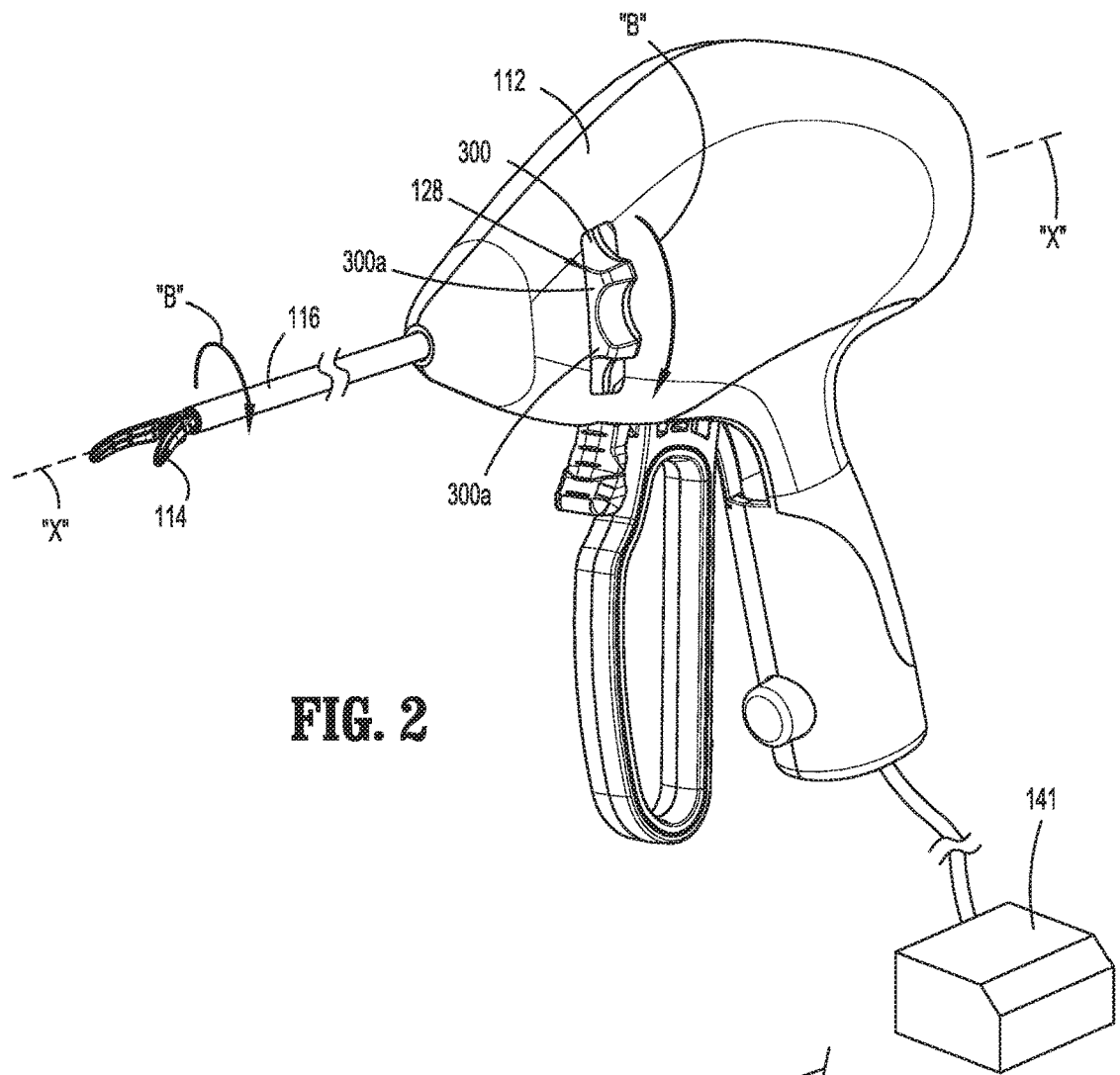
FIG. 2 is a perspective view of the electrosurgical forceps of FIG. 1A.
Figure 3:
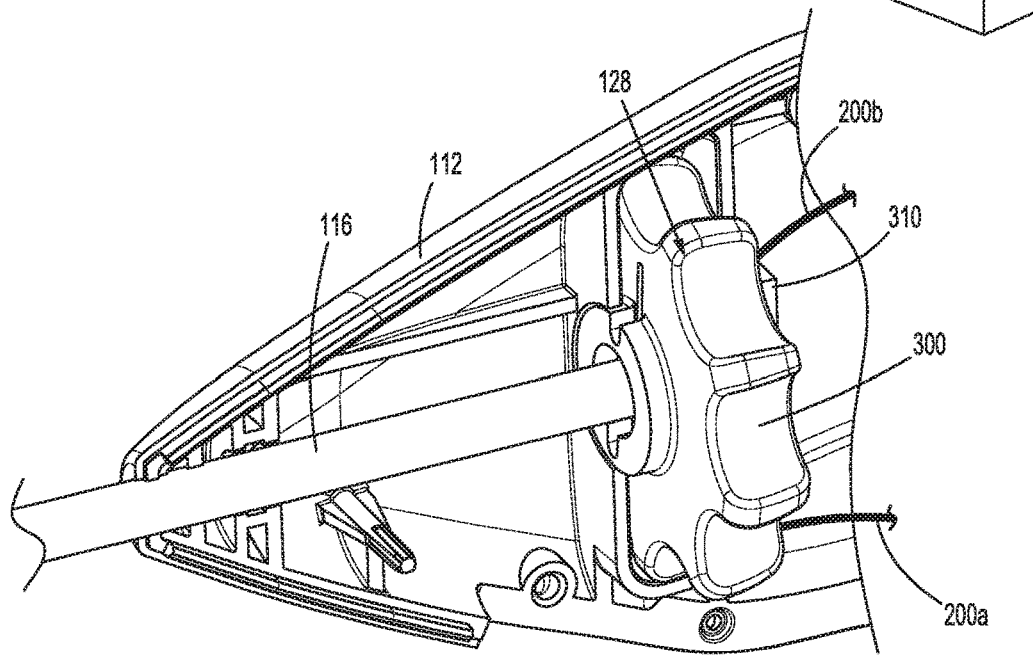
FIG. 3 is an enlarged, perspective view of a portion of the electrosurgical forceps of FIG. 1A and illustrating internal components thereof.

End effector 114 of electrosurgical forceps 100 may be moved from the open position (FIG. 1B), in which tissue (not shown) can be received between jaw members 130, 132 of end effector 114, and the closed position (FIG. 1C), in which tissue can be clamped and treated with electrosurgical energy delivered from generator 141. Jaw members 130, 132 pivot about a pivot pin 144 to move end effector 114 to the closed position (FIG. 2B) in which sealing plates 150, 148 of respective jaw members 130, 132 provide a pressure to tissue grasped between jaw members 130, 132. In some embodiments, to provide an effective tissue seal, a pressure within a range between about 3 kg/cm$^2$ to about 16 kg/cm$^2$ and, desirably, within a working range of about 7 kg/cm$^2$ to about 13 kg/cm$^2$, may be applied by end effector 114 to the tissue. Also, in the closed position, a separation or gap distance is maintained between the sealing plates 148, 150 by an array of stop members 154 (FIG. 1B) disposed on or adjacent to sealing plates 148, 150. Stop members 154 contact opposing surfaces of jaw member 130, 132 and prevent further approximation of sealing plates 148, 150. In some embodiments, to provide an effective tissue seal, an appropriate gap distance of about 0.001 inches to about 0.010 inches and, desirably, between about 0.002 inches to about 0.005 inches, may be provided. In some embodiments, stop members 154 are constructed of a heat-resistant ceramic deposited onto jaw members 130, 132. In other embodiments, stop members 154 are constructed of an electrically non-conductive plastic molded onto jaw members 130, 132 by a process such as overmolding or injection molding, for example. Stop members 154 may be provided in any suitable number, arrangement, and/or configuration.

Upper and lower jaw members 130, 132 of end effector 114 are electrically coupled to generator 141 to provide an electrical pathway to opposed tissue-engaging sealing plates 148, 150 of lower and upper jaw members 132, 130, respectively. In some embodiments, sealing plates 148 and 150 are electrically coupled to opposite terminals, for example, positive or active (+) and negative or return (−) terminals associated with generator 141 so that bipolar energy may be provided through sealing plates 148, 150 to tissue. Alternatively, sealing plates 148, 150 may be configured to deliver monopolar energy to tissue. In a monopolar configuration, one or both sealing plates 148, 150 deliver electrosurgical energy from an active terminal (+) while a return pad (not shown) is placed generally on a patient and provides a return path to the opposite terminal (−) of generator 141.

Electrosurgical energy may be delivered to tissue through electrically conductive seal plates 148, 150 to effect a tissue seal. Once a tissue seal is established, a knife blade 156 having a sharpened distal edge 157 may be advanced through a knife channel 158 defined in one or both jaw members 130, 132 to transect sealed tissue. Although knife blade 156 is depicted in FIG. 1B as extending from elongated shaft assembly 116 when end effector 114 is in an open position, in some embodiments, extension of knife blade 156 into knife channel 158 when end effector 114 is in the open position is prevented.

For a more detailed description of a similar electrosurgical forceps, or components thereof, reference can be made, for example, to U.S. Pat. No. 9,655,673 to McCullough, Jr. et al. and U.S. Pat. No. 9,820,765 to Allen et al., the entire contents of each of which are incorporated herein by reference.

Referring now to FIGS. 2-14, rotation knob assembly 128 of electrosurgical forceps 100 is supported in instrument housing 112 of electrosurgical forceps 100 and is secured to elongated shaft assembly 116 thereof. Rotation knob assembly 128 includes a rotation knob 300 that is rotatably coupled to an inner housing assembly 310. Inner housing assembly 310 of rotation knob assembly 128 is secured to instrument housing 112. In general, rotation knob 300 of rotation knob assembly 128 is selectively rotatable relative to instrument housing 112, as indicated by arrows "B," to rotate elongated shaft assembly 116 and end effector 114 about longitudinal axis "X-X" of electrosurgical forceps 100. Rotation knob 300 has a plurality of spaced-apart fingers 300a that extends radially outward therefrom to facilitate gripping and manual rotation of rotation knob 300. Inner housing assembly 310 of rotation knob assembly 128 is electrically coupled to generator 141 via wires 200a, 200b to transmit electrical energy through rotation knob assembly 128 to end effector 114 in any rotational position of rotation knob 300, elongated shaft assembly 116, and/or end effector 114 relative to inner housing assembly 310.

Rotation knob 300 of rotation knob assembly 128 is supported in instrument housing 112 of electrosurgical forceps 100 and extends radially outward from opposing sides of instrument housing 112 (see FIG. 2—only one side shown) to facilitate user access to fingers 300a of rotation knob 300. Rotation knob 300 includes a shaft mount 302 that extends distally therefrom (see FIG. 3) for coupling to elongated shaft assembly 116.

Figure 4:
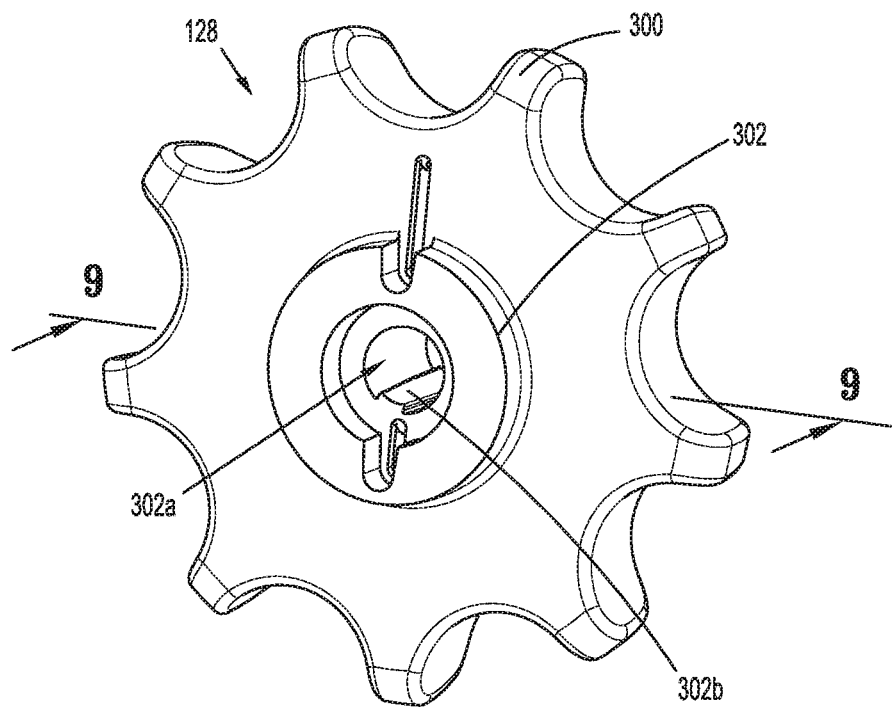
FIG. 4 is an enlarged, front view of a rotation knob assembly of the electrosurgical forceps of FIG. 1A.
Figure 5:
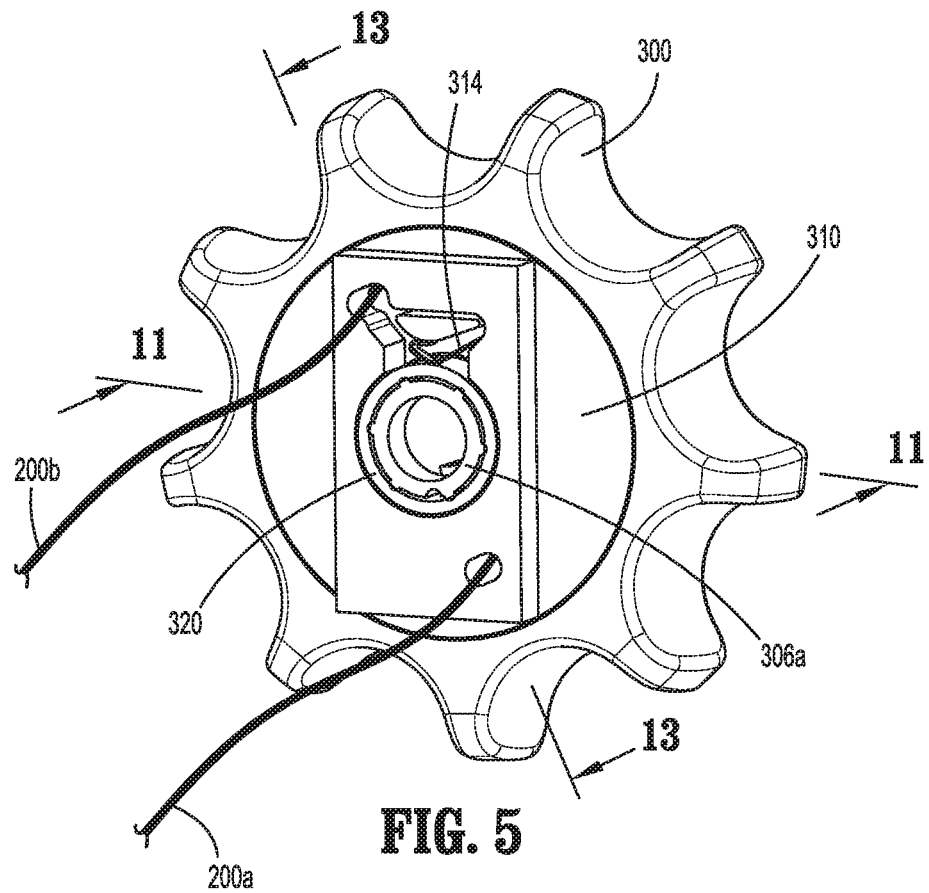
FIG. 5 is a rear view of the rotation knob assembly of FIG. 4 with wires shown coupled thereto.

As seen in FIG. 4, shaft mount 302 of rotation knob 300 includes a passageway 302a defined therethrough for receiving elongated shaft assembly 116 of electrosurgical forceps 100 therein. Passageway 302a has a generally circular profile corresponding to a generally circular profile of elongated shaft assembly 116. Passageway 302a includes a longitudinal key 302b that aligns with, and seats within, a longitudinal slot (not shown) defined within a bottom surface of elongated shaft assembly 116 to enable elongated shaft assembly 116 to rotate with rotation knob 300. In particular, longitudinal key 302b projects radially inward along a length of passageway 302b such that insertion of elongated shaft assembly 116 into passageway 302a of rotation knob 300 operatively couples elongated shaft assembly 116 to rotation knob 300. In some embodiments, longitudinal key 302b may extend from elongated shaft assembly 116 and passageway 302a is configured to receive the longitudinal key that extends from the elongated shaft assembly. Rotation knob 300 is configured to impart rotational motion to elongated shaft assembly 116 and end effector 114 upon rotation of rotation knob 300 about longitudinal axis "X-X" of forceps 100.

Figure 6:
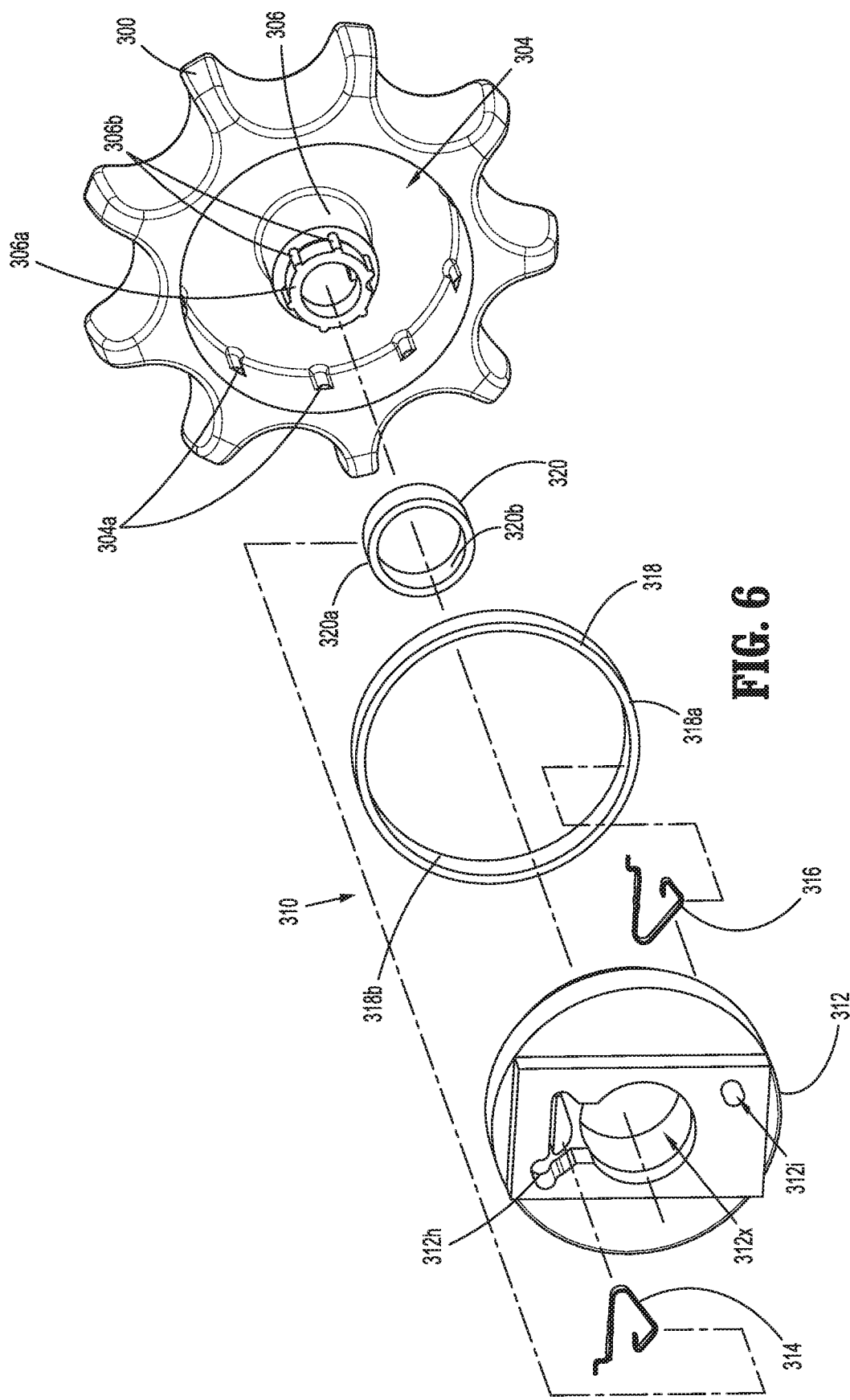
FIG. 6 is a perspective view, with parts separated, of the rotation knob assembly of FIG. 4.
Figure 7:
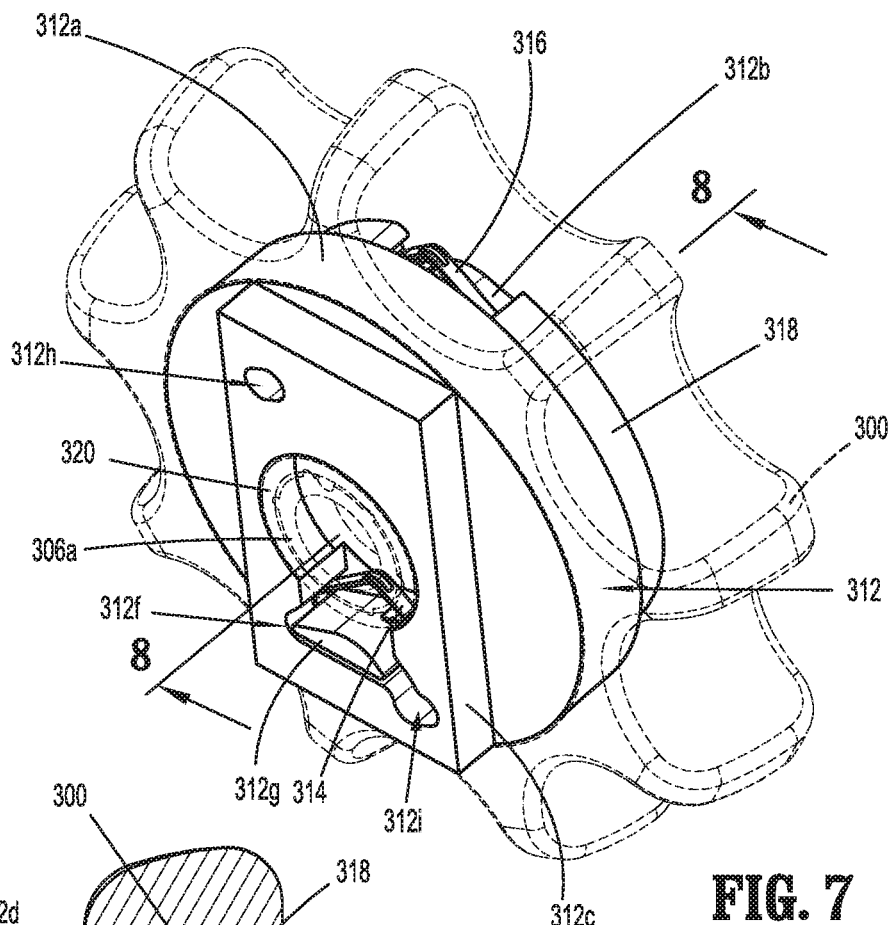
FIG. 7 is an enlarged, perspective view of the rotation knob assembly of FIG. 4 with a rotation knob of the rotation knob assembly shown in phantom for clarity.
Figure 8:
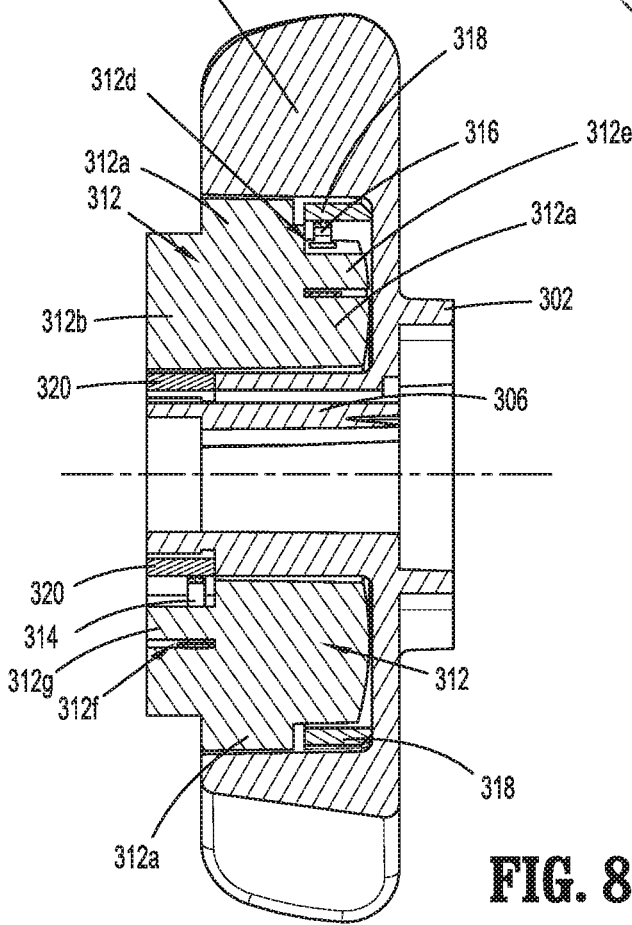
FIG. 8 is an enlarged, cross-sectional view of the rotation knob assembly of FIG. 4 taken along section line 8-8 of FIG. 7.
Figure 9:
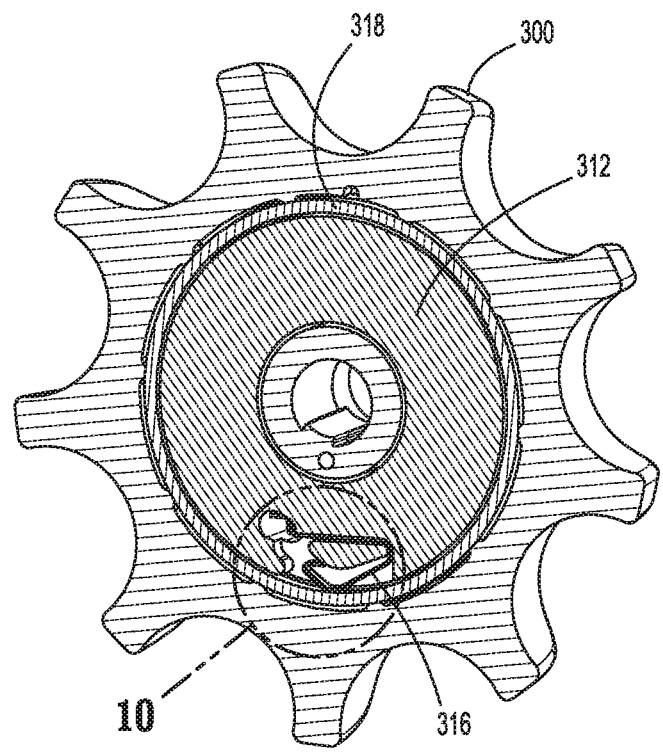
FIG. 9 is a cross-sectional view of the rotation knob assembly of FIG. 4 taken along section line 9-9 of FIG. 4.
Figure 10:
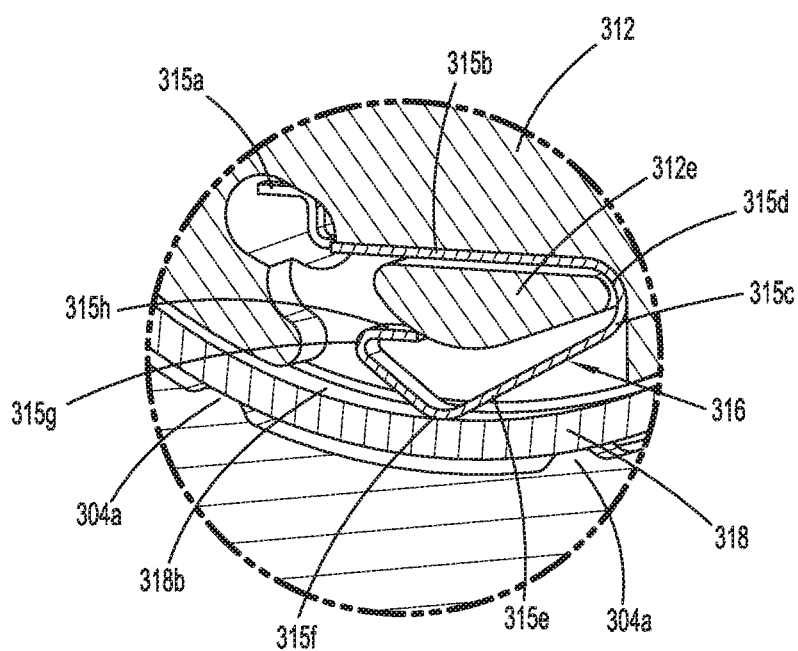
FIG. 10 is an enlarged, perspective view of the indicated area of detail shown in FIG. 9.
Figure 11:
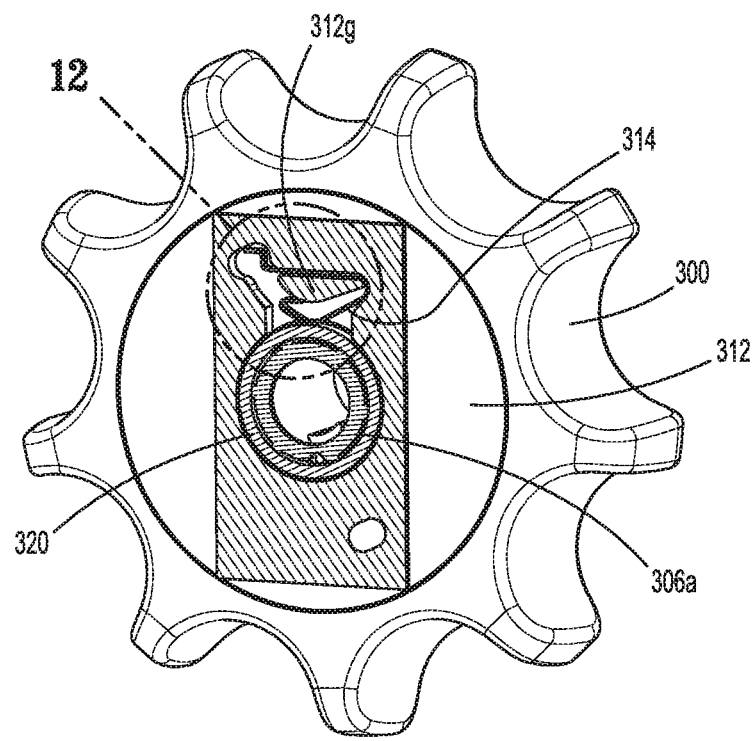
FIG. 11 is a cross-sectional view of the rotation knob assembly of FIG. 4 taken along section line 11-11 of FIG. 5.
Figure 12:
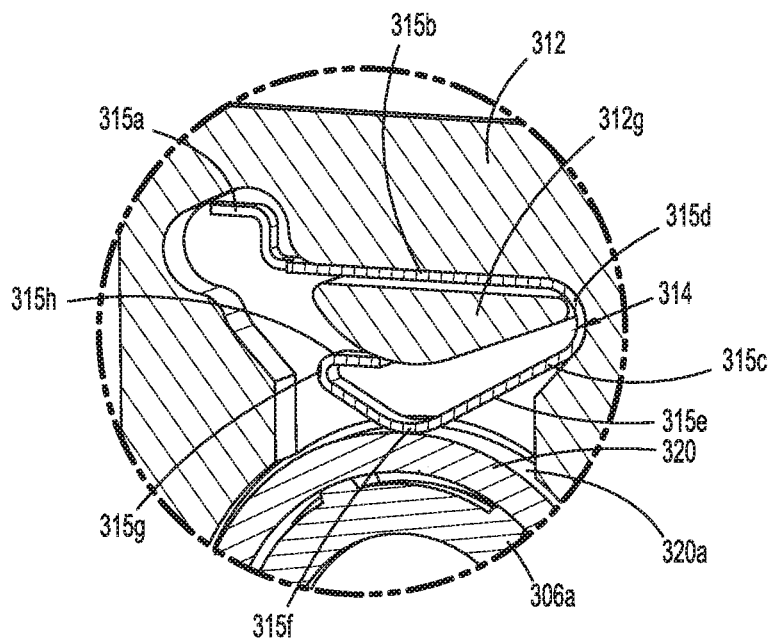
FIG. 12 is an enlarged, perspective view of the indicated area of detail shown in FIG. 11.
Figure 13:
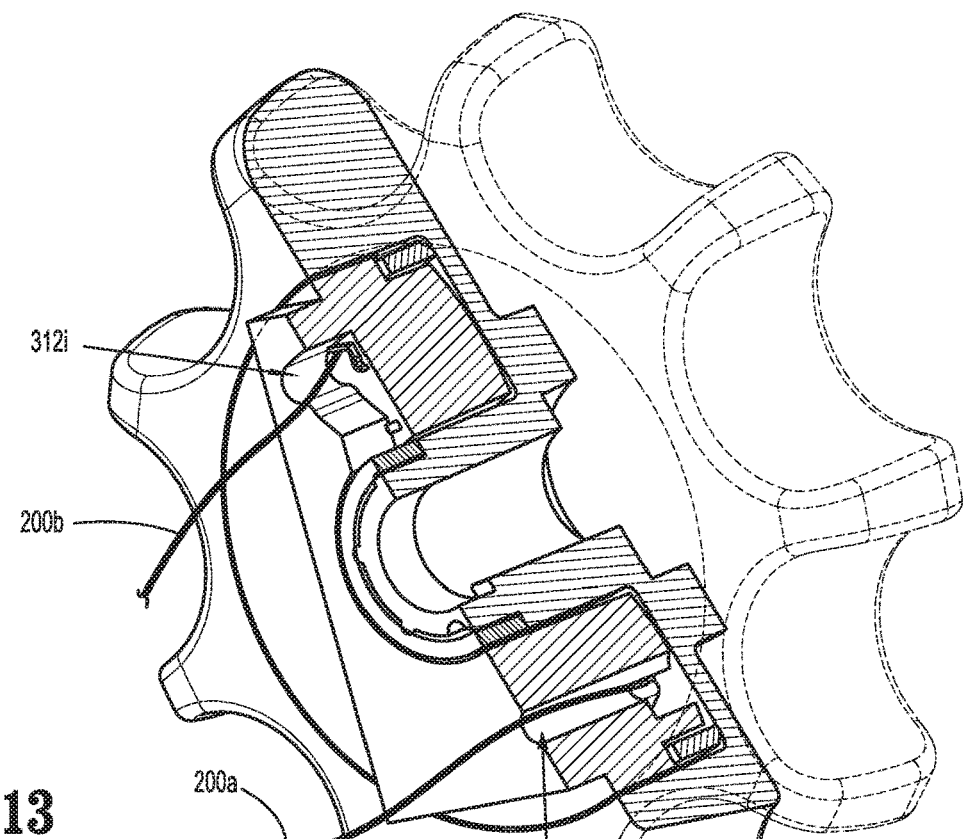
FIG. 13 is an enlarged, cross-sectional view of the rotation knob assembly and wires of FIG. 5, taken along section line 13-13, and with portions of the rotation knob assembly shown in phantom for clarity.
Figure 14:
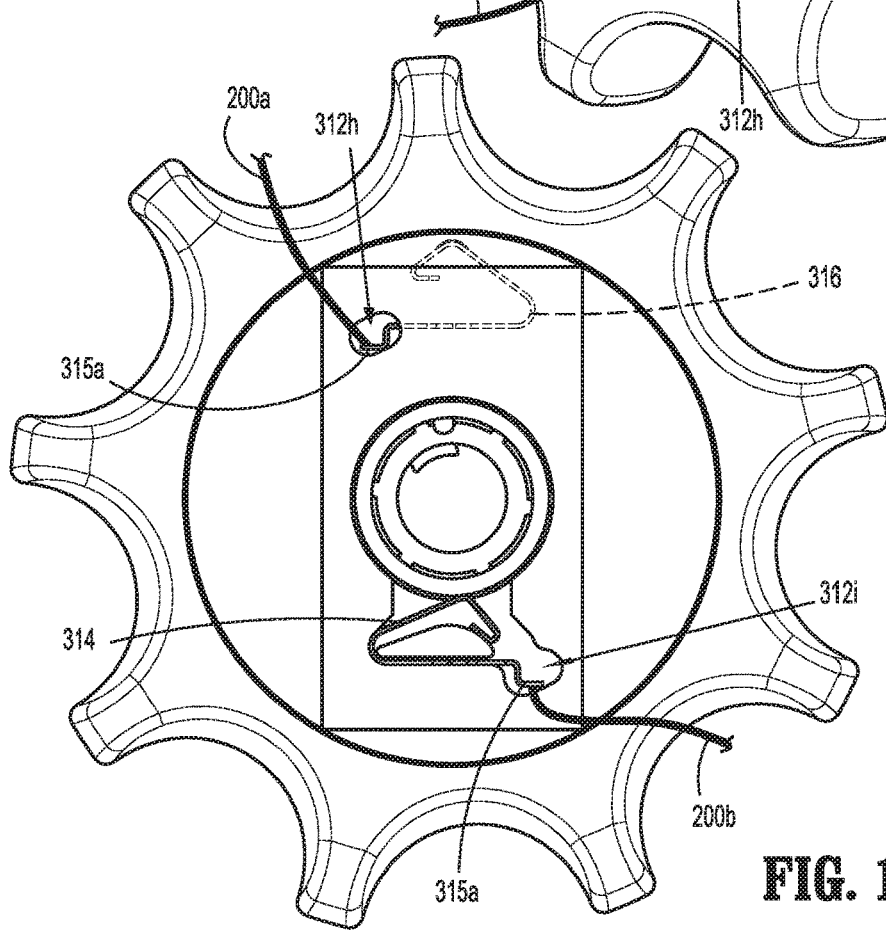
FIG. 14 is an enlarged, rear view of the rotation knob assembly of FIG. 5 and with wires shown.

As best seen in FIG. 6, rotation knob 300 of rotation knob assembly 128 defines an annular opening 304 in a proximal surface thereof for receiving internal components of rotation knob assembly 128. Rotation knob 300 also includes a knob mount 306 that extends proximally through annular opening 304 for supporting internal components of rotation knob assembly 128 within annular opening 304 of rotation knob 300. Rotation knob 300 further includes a plurality of spaced apart ribs 304a that extend into annular opening 304 around an outer circumference thereof to support outer contact ring 318. Knob mount 306 supports an inner ring mount 306a that has a plurality of spaced-apart struts 306b positioned about an outer circumference of inner ring mount 306a to support inner contact ring 320 thereon. In some embodiments, rotation knob 300 and/or inner ring mount 306a have no ribs and/or struts, but are configured to support contact rings 318, 320 by press-fit or the like.

With continued reference to FIGS. 6-12, inner housing assembly 310 of rotation knob assembly 128 includes an inner housing 312, a first contact spring 314, a second contact spring 316, an outer contact ring 318, and inner contact ring 320. Inner housing 312 of inner housing assembly 310 is formed of any suitable non-conductive material (e.g., polymeric material) and defines a central opening 312x that receives knob mount 306 of rotation knob 300 and inner contact ring 320 of inner housing assembly 310 therein to couple inner housing assembly 310 and rotation knob 300 together. Inner housing 312 includes a central plate 312a having a distal projection 312b and a proximal projection 312c that extend in opposite directions from central plate 312a. Distal projection 312b defines a contact spring channel 312d around a distal jut 312e extending distally from central plate 312a. Contact spring channel 312d supports second contact spring 316 therein. Proximal projection 312c defines a contact spring channel 312f around a proximal jut 312g extending proximally from central plate 312a. Each of distal and proximal juts 312e, 312g may have a curvilinear and/or oblong profile configured to accommodate first and second contact springs 314, 316, respectively. Proximal projection 312c further defines cable openings 312h, 312i configured to receive wires 200a, 200b therein, respectively, for electrically coupling wires 200a, 200b to wire connector arms 315a of first and second contact springs 314, 316, respectively (see FIGS. 13 and 14).

Outer contact ring 318 of inner housing assembly 310, which is longitudinally spaced-apart from inner contact ring 320 of inner housing assembly 310, includes an outer surface 318a and an inner surface 318b. Inner contact ring 320, which has a diameter smaller than outer contact ring 318 and is provided in a different plane than outer contact ring 318, also includes an outer surface 320a and inner surface 320b. Inner and outer contact rings 320, 318 are electrically coupled to end effector 114 through elongated shaft assembly 116 and may have any suitable cylindrical configuration.

With reference to FIGS. 6-14, first and second contact springs 314, 316 of inner housing assembly 310 may be identical, and may be formed of any suitable conductive material (e.g., metallic material). Each of first and second contact springs 314, 316 may have any suitable geometric shape. For instance, in embodiments, each contact spring may include a wire connector arm 315a, which may be L-shaped, a straight arm 315b that extends from wire connector arm 315a to a hooked arm 315c. Hooked arm 315c is coupled to straight arm 315b by a first bend 315d that extends to a straight segment 315e. Straight segment 315e extends to an elbow 315f. Elbow 315f extends to a hook 315g. Hook 315g includes a tooth 315h. Tooth 315h of first contact spring 314 engages proximal jut 312g and elbow 315f of first contact spring 314 contacts outer surface 320a of inner contact ring 320. Tooth 315h of second contact spring 316 engages distal jut 312e, and elbow 315f of second contact spring 316 contacts inner surface 318b of outer contact ring 318. First and/or second contact springs 314, 316 may be in the form of any suitable spring connector such as a pogo pin, SIB, or the like, and may have any suitable shape and/or configuration.

With reference to FIGS. 2-14, in use, rotation knob 300 is rotated, as indicated by arrows "B" (FIG. 2), to rotate elongated shaft assembly 116 as rotation knob 300 rotates about inner housing assembly 310. Advantageously, elongated shaft assembly 116 and end effector 114 can rotate relative wires 200a, 200b so as to enable continuous, or infinite rotation of elongated shaft assembly 116 and end effector 114. In particular, wires 200a, 200b are coupled to outer and inner contact rings 318, 320 through first and second contact springs 314, 316, respectively, in an electrically isolated manner such that electrical energy can be selectively delivered through rotation knob assembly 128 while rotation knob assembly 128 provides infinite rotation of elongated shaft assembly 116 and end effector 114.

Turning now to FIGS. 15-20, another embodiment of a rotation knob assembly, generally referred to as rotation knob assembly 400, is provided and is similar in operation and construction to rotation knob assembly 128.

More particularly, rotation knob assembly 400 includes a rotation knob 401 having a first knob half 402 and a second knob half 404. First knob half 402 defines pin recesses 402a that receive pins 404a of second knob half 404 to couple first and second knob halves 402, 404 together to house an inner housing 406, an inner contact ring 408, an outer contact ring 410, a first contact spring 412, and a second contact spring 414 therein. First knob half 402 further includes a shaft mount 402b that extends therefrom to secure to elongated shaft assembly 116 (see FIG. 1A). First knob half 402 further includes an outer ring recess 402c and an inner ring recess 402d defined therein and separated by an isolation ring 402e. Outer contact ring 410 is received within outer ring recess 402c of first knob half 402 and inner contact ring 408 is received in inner ring recess 402d of first knob half 402 such that inner and outer rings 408, 410 are electrically isolated from one another. Second knob half 404 further includes an inner annular rib 404c that is engageable with inner housing 406.

Inner contact ring 408 of rotation knob assembly 400 includes a contact face 408a and radial tabs 408b that extend radially inward from inner contact ring 408 to support inner contact ring 408 within inner ring recess 402d of first knob half 402. Inner contact ring 408 further includes an arm 408c that extends transversely from inner contact ring 408 and supports an electrical connector 408d configured to couple to an electrical wire in electrical communication with end effector 114 of forceps 100 through elongated shaft assembly 116 (FIG. 1A) of forceps 100.

Outer contact ring 410 of rotation knob assembly 400 includes a contact face 410a and radial tabs 410b that extend radially outward from outer contact ring 410 to support outer contact ring 410 within outer ring recess 402c of first knob half 402. Outer contact ring 410 further includes an arm 410c that extends transversely from outer contact ring 410 and supports an electrical connector 410d configured to couple to an electrical wire in electrical communication with end effector 114 of forceps 100 through elongated shaft assembly 116 (FIG. 1A) of forceps 100.

Figure 15:
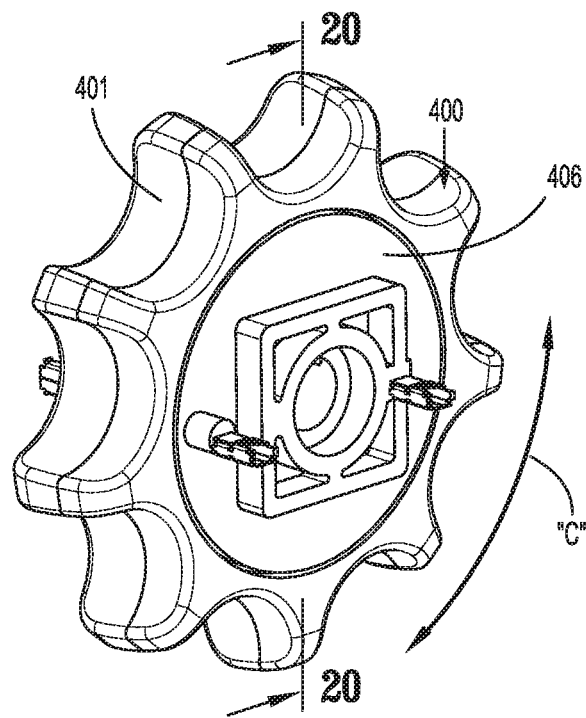
FIG. 15 is a rear, perspective view of another embodiment of a rotation knob assembly of the electrosurgical forceps of FIG. 1A.
Figure 16:
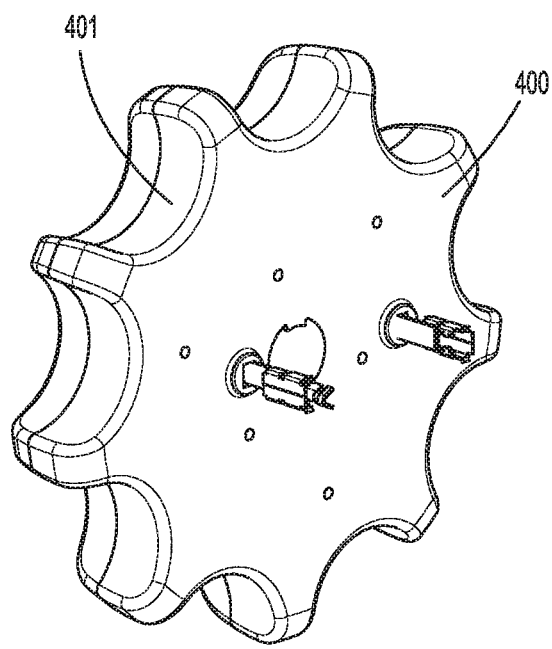
FIG. 16 is a front, perspective view of the rotation knob assembly of FIG. 15.
Figure 17:
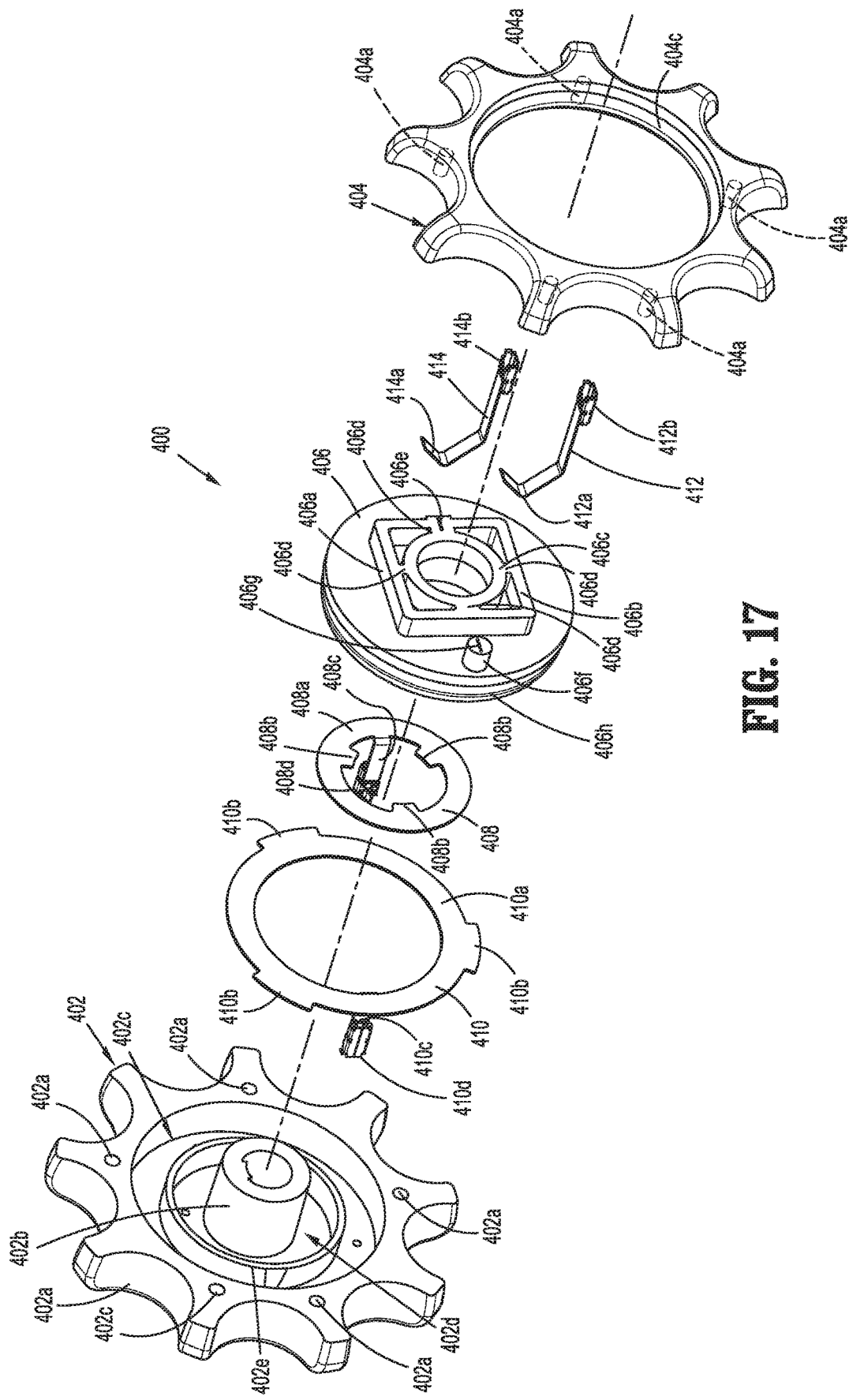
FIG. 17 is a rear, perspective view, with parts separated, of the rotation knob assembly of FIGS. 15 and 16.
Figure 18:
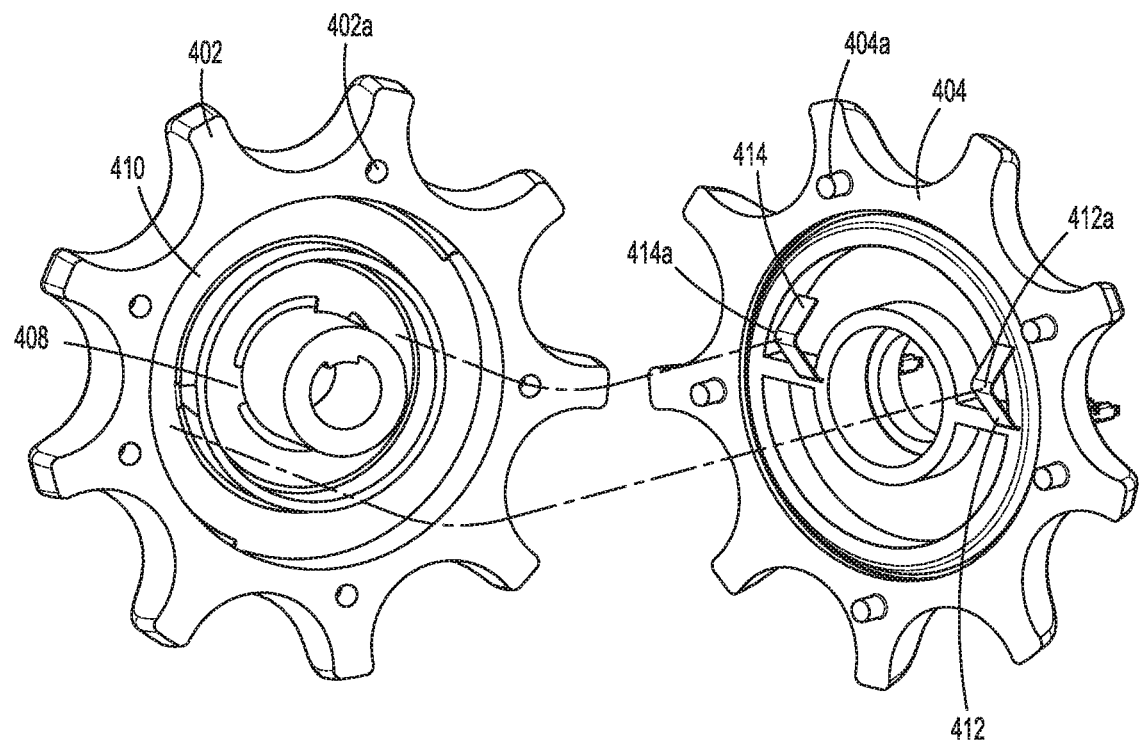
FIG. 18 is a perspective view, with parts separated, of the rotation knob assembly of FIGS. 15 and 16.
Figure 19:
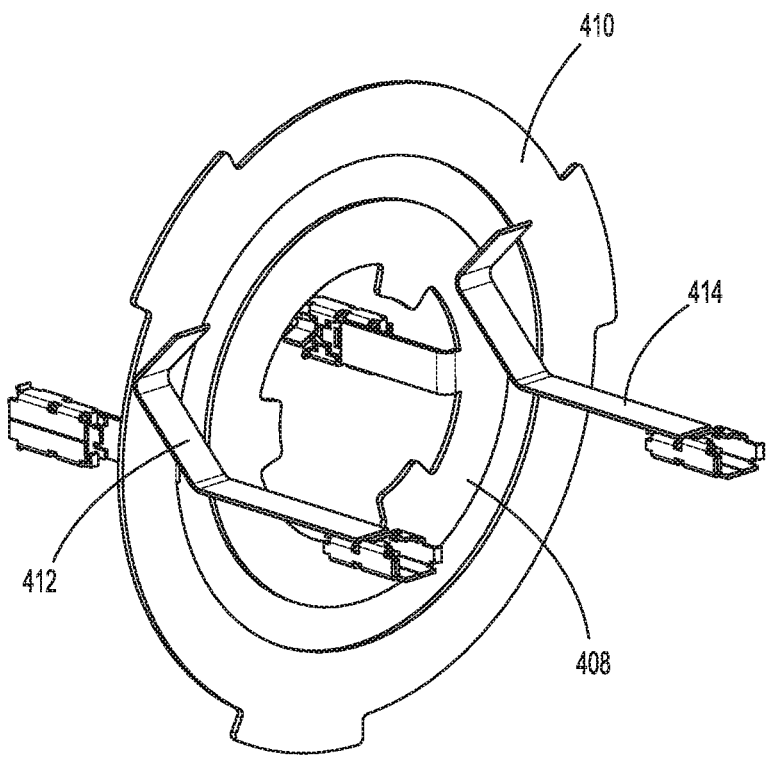
FIG. 19 is an enlarged, perspective view of FIG. 15 with portions thereof removed for clarity.
Figure 20:
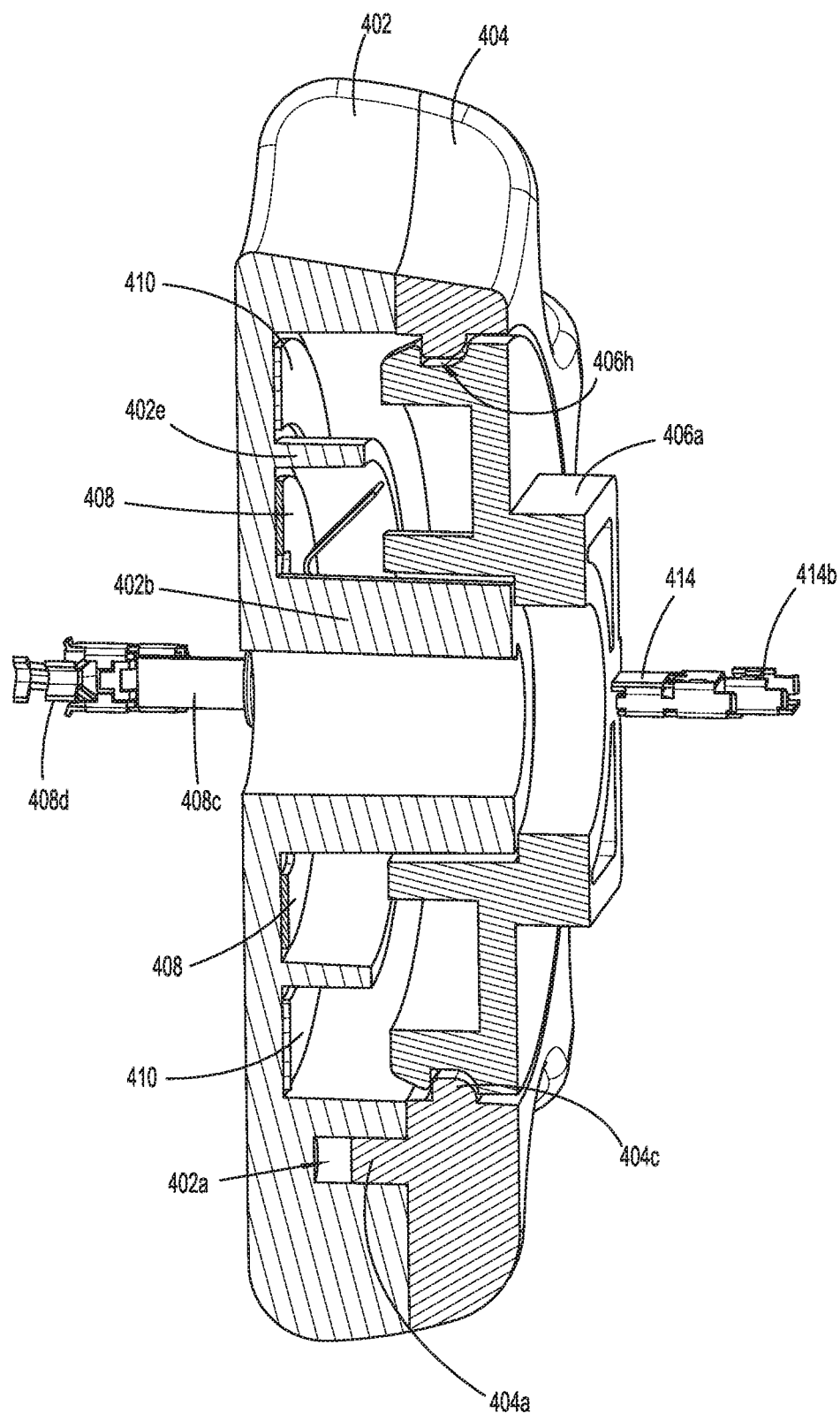
FIG. 20 is an enlarged, cross-sectional view of FIG. 15 taken along section line 20-20 of FIG. 15.

Inner housing 406 of rotation knob assembly 400 includes a first projection 406a having an outer box 406b and an inner tube 406c. Outer box 406b and inner tube 406c are connected by fingers 406d. First projection 406a further defines a slot 406e therethrough for receiving second contact spring 414 therein and aligning second contact spring 414 with inner contact ring 408. Inner housing 406 also includes a second projection 406f that defines a slot 406g therethrough for receiving first contact spring 412 and aligning first contact spring 412 with outer contact ring 410. Inner housing 406 further includes an outer annular channel 406h defined therein that receives annular rib 404c of knob half 404 to enable rotation knob 401 to rotate about inner housing 406, as indicated by arrow "C" (FIG. 15).

First contact spring 412 of rotation knob assembly 400 includes an elbow 412a that is positioned to engage contact face 410a of outer contact ring 410 to facilitate electrical communication therethrough. Second contact spring 414 of rotation knob assembly 400 includes an elbow 414a that is positioned to engage contact face 408a of inner contact ring 408 to facilitate electrical communication therethrough. Each of first and second contact springs 412, 414 support electrical contacts 412b, 414b, respectively, to facilitate electrical connection with wires such as wires 200a, 200b (see FIG. 3).

Figure 21:
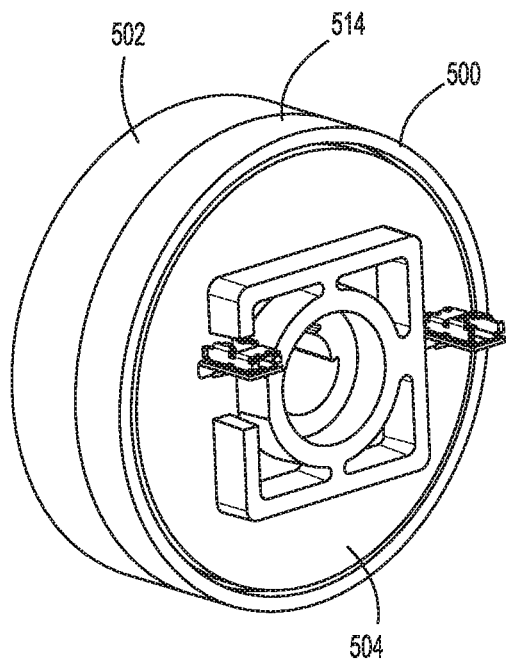
FIG. 21 is a rear, perspective view of yet another embodiment of a rotation knob assembly of the electrosurgical forceps of FIG. 1A.
Figure 22:
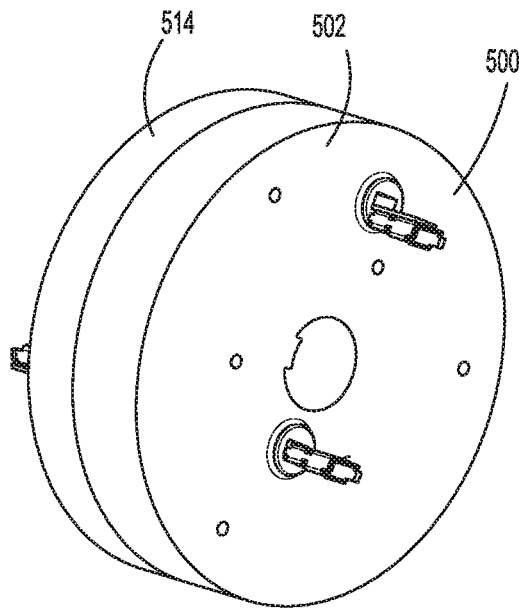
FIG. 22 is a front, perspective view of the rotation knob assembly of FIG. 21.
Figure 23:
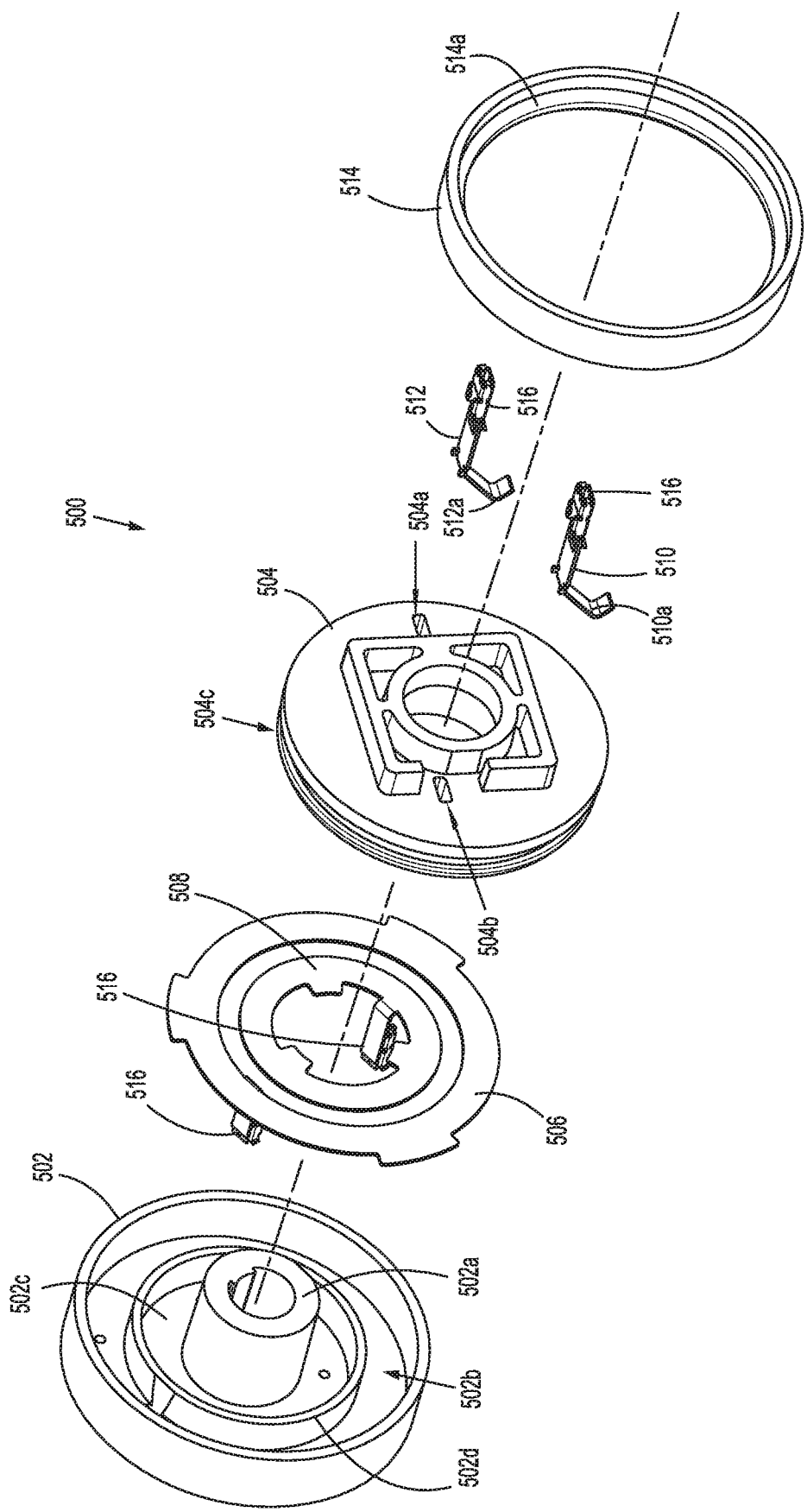
FIG. 23 is a rear, perspective view, with parts separated, of the rotation knob assembly of FIGS. 21 and 22.

Turning now to FIGS. 21-23, another embodiment of a rotation knob assembly, generally referred to as rotation knob assembly 500, is provided and is similar in operation and construction to rotation knob assemblies 128, 400. Rotation knob assembly 500 is configured for autonomous moment (e.g., powered and/or robotically controlled) and can be enclosed within instrument housing 112 of electrosurgical forceps 100. In general, rotation knob assembly 500 includes an outer housing 502, an inner housing 504, an outer contact ring 506, an inner contact ring 508, a first contact spring 510, a second contact spring 512, and a ring housing 514. Outer contact ring 506, inner contact ring 508, first contact spring 510, and second contact spring 512 include wire connectors 516 that are configured to operatively couple to wires such as wires 200a, 200b (see FIG. 3).

Outer housing 502 of rotation knob assembly 500 includes a shaft mount 502a and defines an outer ring recess 502b and an inner ring recess 502c therein that are separated by an isolation ring 502d. Outer contact ring 506 is received in outer ring recess 502b and inner contact ring 506 is received in inner ring recess 502c. Inner housing 504 of rotation knob assembly 500 is supported on shaft mount 502a and defines a first slot 504a and a second slot 504b therethrough. First slot 504a is positioned to receive contact spring 512 and second slot 504b is positioned to receive contact spring 510 to facilitate electrical communication through rotation knob assembly 500. Contact spring 510 includes an elbow 510a that is positioned to engage outer contact ring 506 and contact spring 512 includes an elbow 512a that is positioned to engage inner contact ring 508.

Ring housing 514 of rotation knob assembly 500 is rotatably supported on inner housing 504 and includes an annular rib 514a that is receivable in an annular channel 504c defined in inner housing 504 to facilitate relative rotation between ring housing 514 and inner housing 504.

In some embodiments, the inner and outer contact rings may be longitudinally aligned and/or positioned in the same plane.

In certain embodiments, first and second contact rings may be radially spaced the same distance from the disclosed shaft assemblies, but with the corresponding contact springs having different orientations relative to one another so that a first contact spring contacts the first ring and a second contact spring contacts the second ring.

In various embodiments, the contact springs may have an asymmetric configuration to facilitate positioning and/or spacing relative to one another within a rotation knob.

As can be appreciated, securement of any of the components of the presently disclosed apparatus can be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. A forceps, comprising:
    an instrument housing;
    an elongated shaft assembly extending distally from the instrument housing and defining a longitudinal axis; and
    a rotation knob assembly supported in the instrument housing and including a rotation knob and an inner housing disposed within the rotation knob, the rotation knob coupled to the shaft assembly and positioned to rotate about the inner housing to rotate the elongated shaft assembly relative to the instrument housing, the inner housing coupled to the instrument housing and supporting electrical contacts configured to transmit electrical energy through the rotation knob assembly, the rotation knob assembly including an inner contact ring and an outer contact ring that are longitudinally offset from one another relative to the longitudinal axis, the inner contact ring disposed in contact with a first contact spring, the outer contact ring disposed in contact with a second contact spring, the first and second contact springs being vertically offset from one another;

wherein the inner contact ring and the outer contact ring are electrically isolated from one another; and wherein the inner contact ring has a diameter and the outer ring contact has a diameter, the diameter of the inner contact ring different from the diameter of the outer contact ring.

2. The forceps of claim 1, wherein the rotation knob defines an outer ring recess positioned to receive the outer contact ring and an inner ring recess positioned to receive the inner contact ring.

3. The forceps of claim 2, wherein the inner and outer ring recesses are separated by an isolation ring.

4. The forceps of claim 1, wherein the first and second contact springs are supported by the inner housing and electrically isolated from one another.

5. The forceps of claim 4, wherein the first contact spring is coupled to a first electrical wire and the second contact spring is coupled to a second electrical wire.

6. The forceps of claim 5, wherein the first and second electrical wires extend through the inner housing and are positioned to enable continuous rotation of the elongated shaft assembly about the longitudinal axis in response to rotation of the rotation knob about the inner housing and about the first and second electrical wires.

7. The forceps of claim 1, wherein the rotation knob includes a shaft mount defining a passageway for receiving the elongated shaft assembly therein.

8. The forceps of claim 1, wherein the first contact spring is radially closer to the longitudinal axis than the second contact spring.

9. An electrosurgical system, comprising:
an energy source; and
a forceps electrically coupled to the energy source, the forceps including:
an instrument housing;
an elongated shaft assembly extending distally from the instrument housing to an end effector, the elongated shaft assembly defining a longitudinal axis;
a rotation knob assembly supported in the instrument housing and including a rotation knob and an inner housing disposed within the rotation knob, the rotation knob coupled to the shaft assembly and positioned to rotate about the inner housing to rotate the elongated shaft assembly relative to the instrument housing, the inner housing coupled to the instrument housing and supporting electrical contacts configured to transmit electrical energy from the energy source through the rotation knob assembly to the end effector, the rotation knob assembly including an inner contact ring and an outer contact ring that are longitudinally offset from one another relative to the longitudinal axis, the inner contact ring disposed in contact with a first contact spring, the outer contact ring disposed in contact with a second contact spring, the first and second contact springs being vertically offset from one another;

wherein the inner contact ring and the outer contact ring are electrically isolated from one another; and wherein the inner contact ring has a diameter and the outer contact ring has a diameter, the diameter of the inner contact ring different from the diameter of the outer contact ring.

10. The electrosurgical system of claimer 9, wherein the rotation knob defines an outer ring recess positioned to receive the outer contact ring and an inner ring recess positioned to receive the inner contact ring.

11. The electrosurgical system of claim 10, wherein the inner and outer ring recesses are separated by an isolation ring.

12. The electrosurgical system of claim 9, wherein the first and second contact springs are supported by the inner housing and electrically isolated from one another by the inner housing.

13. The electrosurgical system of claim 9, wherein the rotation knob includes a shaft mount defining a passageway for receiving the elongated shaft assembly therein.

14. The electrosurgical system of claim 9, wherein the first contact spring is radially closer to the longitudinal axis than the second contact spring.

15. The electrosurgical system of claim 9, wherein the first contact spring is coupled to a first electrical wire and the second contact spring is coupled to a second electrical wire, the first and second electrical wires connected to the energy source, the first and second contact springs disposed in electrical communication with the end effector to enable the first and second wires to transmit electrical energy from the energy source to the end effector.

16. The electrosurgical system of claim 15, wherein the first and second electrical wires extend through the inner housing and are positioned to enable continuous rotation of the elongated shaft assembly about the longitudinal axis in response to rotation of the rotation knob about the inner housing and about the first and second electrical wires.

* * * * *